United States Patent [19]

Hussain

[11] Patent Number: 5,081,316
[45] Date of Patent: Jan. 14, 1992

[54] MELTING POINT ENHANCEMENT OF PARTIALLY BROMINATED DIPHENYL OXIDE MIXTURES

[75] Inventor: Saadat Hussain, Baton Rouge, La.

[73] Assignee: Ethyl Corporation, Richmond, Va.

[21] Appl. No.: 457,849

[22] Filed: Dec. 27, 1989

[51] Int. Cl.$^5$ .............................................. C07C 43/29
[52] U.S. Cl. .................................. 568/639; 252/601; 252/609
[58] Field of Search ................ 568/639, 635; 252/601, 252/609

[56] References Cited

U.S. PATENT DOCUMENTS

| | | | |
|---|---|---|---|
| 3,959,387 | 5/1976 | Brackenridge | 568/639 |
| 4,521,633 | 6/1985 | Pedjac | 568/639 |
| 4,847,428 | 7/1989 | Gu | 568/639 |
| 4,871,882 | 10/1989 | Stollar et al. | 568/639 |

Primary Examiner—Robert L. Stoll
Assistant Examiner—Joseph D. Anthony
Attorney, Agent, or Firm—E. E. Spielman, Jr.

[57] ABSTRACT

This invention relates to a process for increasing the melting point of partially brominated diphenyl oxide mixtures having an average bromine content of 7.0 to 8.5. The process comprises: forming a slurry comprised of alkyl halide and the mixture; and evaporating essentially all of the allyl halide from the slurry.

9 Claims, No Drawings

MELTING POINT ENHANCEMENT OF PARTIALLY BROMINATED DIPHENYL OXIDE MIXTURES

BACKGROUND OF THE INVENTION

This invention relates to a process for increasing the melting point of mixtures of partially brominated diphenyl oxides having an average of 7.0 to 8.5 bromine atoms per molecule of diphenyl oxide.

The above mixtures are sold and denominated by the flame retardant industry as octabromodiphenyl oxide or as "Octabrom". For the sake of simplicity, these mixtures will hereinafter be referred to as Octabrom. Typically, the commercially significant Octabroms contain 0-2 weight percent pentabromodiphenyl oxide, 5-15 weight percent hexabromodiphenyl oxide, 40-55 weight percent heptabromodiphenyl oxide, 30-40 weight percent octabromodiphenyl oxide, 5-15 weight percent nonabromodiphenyl oxide, and 0-2 weight percent decabromodiphenyl oxide. As can be appreciated, for any particular Octabrom, the average number of bromine atoms per molecule of brominated diphenyl oxide, hereinafter referred to as the average bromine number, is dependent upon the amounts and the identities of the particular bromo homologs which are present in the mixture. The average bromine number can be calculated by multiplying the weight percent of each bromo homolog by the number of bromine atoms in that homolog, adding the resulting products and dividing the sum by 100.

Octabrom has a melting point which is expressed as a temperature range since it does not exhibit a sharp melting point. Depending upon constituents and their amounts of the Octabrom and upon the process and any post-process treatment used for producing the Octabrom, the melting point can be low, e.g., mp 75° C.–95° C., high, e.g., mp 90° C.–145° C. or can be somewhere in-between.

It has been observed that the melting point of any particular Octabrom is an indicator of its amorphic or crystal-line nature. The lower melting Octabroms are much less crystal-line, i.e., more amorphic, than the higher melting Octabroms. Another difference between Octabroms with the lower melting points and Octabroms with the higher melting points is that the former has a tendency to form lumps and not to be free-flowing after being subjected to long storage periods, say a few weeks, and to elevated temperatures, e.g., 50° C. to 80° C.

Besides being an indication of the amorphic or crystal-line nature of Octabrom and the tendency of the Octabrom to lump, the Octabrom melting point can also be a specification set by the Octabrom purchaser. Depending upon the use of the Octabrom, low melt or high melt Octabrom can be required.

THE INVENTION

This invention provides a process for treating Octabrom to raise its melting point. The process comprises: (i) forming a slurry of an alkyl halide and the Octabrom to be treated, the melting point of the Octabrom being greater than the boiling point of the alkyl halide and the Octabrom being essentially insoluble in the alkyl halide at the process temperature; and (ii) evaporating substantially all of the alkyl halide from the slurry to obtain the treated Octabrom.

For the purposes of this invention, it is to be understood that an increase in the Octabrom melting point is deemed to have been achieved when the treated Octabrom has a melting point in which the lowest temperature, the highest temperature or both the highest and lowest temperatures, which define the treated Octabrom's melting point, are greater than the corresponding temperature(s) which define the melting point of the untreated Octabrom. It is also to be realized that there is a practical limit to the melting point increase which can be achieved by the process of this invention, for example, it may be impractical to exceed a lowest temperature of 125° C. and a highest temperature of 140° C.

The process of this invention is most useful in treating Octabrom having a relatively low melting point, for example, an Octabrom having a melting point in which the lowest temperature in the melting point range is from about 65° C. to about 86° C. and in which the highest temperature in the range is from about 95° C. to about 120° C. The value of such a treatment is that the low melting Octabrom is changed from one which can have a lumping problem, above discussed, to one in which the lumping problem is diminished or rendered non-existent.

In addition to treating low melt Octabrom for the lumping problem, the process of this invention is of value in treating Octabrom having a higher melting point, say, one in which the lowest temperature in the melting point range is from about 87° C. to about 100° C. and in which the highest temperature in the range is from about 120° C. to about 135° C. While this Octabrom will generally not have a lumping problem, it still may be desirable to treat such an Octabrom so as to increase its melting point to meet a purchaser's higher melting point specifications.

The alkyl halides used in forming the slurry are preferably alkyl chlorides containing 1 to 2 carbon atoms. Preferred are, methylene chloride, carbon tetrachloride, chloroform and ethylene dichloride. The choice of the particular alkyl halide must taken into consideration the before recited criteria relative to (i) the melting point of the Octabrom to be treated and the boiling point of the selected alkyl halide, and (ii) the substantial insolubility of the Octabrom in the selected alkyl halide. A most highly preferred alkyl halide is methylene chloride, especially when the Octabrom to be treated is a low melting Octabrom.

The degree of the Octabrom's insolubility in the alkyl halide will be different for various of the alkyl halides. But in no case should the solubility exceed 5 grams/100 grams of alkyl halide at 23° C. Due to this low solubility, there is little difference in the bromo homolog distribution between the untreated Octabrom and the treated Octabrom. Thus, product specifications are not adversely affected. Further, the low solubility results in there being insignificant Octabrom loss (<1 weight percent) from use of the process of this invention.

The slurry can be formed by adding the alkyl halide to the Octabrom or vice versa, there being no criticality accorded to the order of addition. The amount of alkyl halide used is that amount which is sufficient to form a readily agitatable slurry. Generally, a slurry containing from about 40 weight percent to about 85 weight percent alkyl halide is suitable, with a slurry containing from about 50 weight percent to about 80 weight percent alkyl halide being most preferred. The foregoing weight percentages are based upon the total weight of the slurry.

The formation of the slurry can conveniently occur at ambient temperature, there being no observed advantage from using higher than ambient temperatures. Temperatures within the range of from about 25° C. to about 85° C. are suitable. Temperatures approaching the alkyl halide boiling point should be avoided as a gum-like substance can be formed. The pressure during the slurry formation is conveniently atmospheric. Sub- and super-atmospheric pressure can also be used but no significant advantage is attributable thereto.

If the Octabrom to be treated is lumpy or of large particle size, it is preferred to grind the Octabrom to a smaller particle size.

During and after the slurry formation, the alkyl halide evaporates from the slurry, with the majority of the alkyl halide evaporating after the slurry is formed. The evaporated alkyl halide can be recovered for reuse as it has been observed to be essentially as pure as the starting alkyl halide. The evaporation can occur at ambient conditions, however, from a process efficiency point of view, it is preferred that an elevated temperature be used after the slurry has been formed. Most highly preferred are those temperatures which are higher than the boiling point of the alkyl halide used but which are not so high as to deleteriously affect the quality of the treated Octabrom. For example, when the alkyl halide is methylene chloride, the most preferred evaporation temperature will be within the range of from about 25° C. to about 45° C.

The pressure used during the evaporation step is not critical, with sub-atmospheric, atmospheric and super-atmospheric pressures being suitable. From a convenience and economical point of view, atmospheric pressure is preferred.

The evaporation period is preferably that period of time which is needed to evaporate essentially all of the alkyl halide from the slurry, e.g. 98% of the alkyl halide used. Less time can be used, but the treated Octabrom can be contaminated with alkyl halide which can adversely affect its melting point range. The evaporation period will be dependent upon the conditions specified for the evaporation step. Higher temperatures result in a shorter evaporation period. Sweeping the evaporated alkyl halide from the evaporation site also aids in shortening the evaporation period.

Octabrom is a commercially available flame retardant which is well known to the art. Octabrom is conventionally produced by reacting bromine, in an amount which is 80 to 100 percent in excess of the stoichiometric amount, with diphenyl oxide in the presence of an iron catalyst.

EXAMPLE I

An Octabrom sample (10 grams) was slurried, at room temperature, in a porcelain dish with 5 mL of methylene chloride. The sample, before slurrying, was a white powder, had a melting point of 114° C.–120° C. and formed a clear liquid at 130° C. After the slurry was obtained the dish was placed in a forced air oven at 72° C. for about 18 hours.

After the 18-hour period in the oven, the sample was removed and allowed to cool. The so-treated Octabrom was a white powder and found to have a melting point of 120° C.–130° C. The treated Octabrom formed a clear liquid at 140° C.

EXAMPLE II

The same procedure was followed as in Example I except that the untreated Octabrom sample had a melting point of 74° C.–84° C. and formed a clear liquid at 106° C. The untreated sample was initially tan colored.

After treatment, the treated Octabrom sample was found to have a melting point 120° C.–126° C. and to form a clear liquid at 140° C. The treated sample was an off-white solid.

EXAMPLE III

A sample of Octabrom (25.0 g) having a melting point of 69° C.–80° C. (clear liquid at 100° C.) was slurried with 13 mL methylene chloride at room temperature in a porcelain dish. The sample had a tan color. The dish was placed under an exhaust hood at room temperature for about 4 hours. The treated sample had a melting point of 108° C.–114° C. and became a clear liquid at 132° C. The sample was then placed in a forced air oven at 78° C. for 2 days. The so-treated sample had a melting point of 118° C.–124° C. and formed a clear liquid at 134° C. The sample color was off-white.

EXAMPLE IV (Comparative Example)

The same procedure of Example III was followed except that the Octabrom sample was not slurried with methylene chloride but rather was simply placed in a porcelain dish.

The sample, after the 2-day period in the oven, had a melting point of 72° C.–84° C. and formed a clear liquid at 112° C. The color of the sample was a dark tan.

The melting point values in Examples I and II were determined conventionally with a capillary melting point instrument.

What is claimed:

1. A process for treating a mixture of partially brominated diphenyl oxides having an average of from about 7.0 to about 8.5 bromine atoms per molecule of diphenyl oxide so as to increase the melting point of the mixture, said process consisting essentially of:
    (a) forming a slurry comprised of an alkyl halide and the mixture to be treated, the melting point of the mixture being greater than the boiling point of the alkyl halide and the mixture being essentially insoluble in the alkyl halide; and
    (b) evaporating essentially all of the alkyl halide from the slurry to obtain the treated mixture.

2. The process of claim 1 wherein the partially brominated diphenyl oxide contains hexabromodiphenyl oxide, heptabromodiphenyl oxide, octabromodiphenyl oxide, nonabromodiphenyl oxide and, optionally, either pentabromodiphenyl oxide, decabromodiphenyl oxide or both pentabromodiphenyl oxide and decabromodiphenyl oxide.

3. The process of claim 1 wherein the alkyl halide is an alkyl chloride containing 1 to 2 carbon atoms.

4. The process of claim 1 wherein the alkyl halide is methylene chloride.

5. The process of claim 1 wherein the alkyl halide comprises from about 40 weight percent to about 85 weight percent of the slurry.

6. The process of claim 4 wherein the methylene chloride comprises from about 40 weight percent to about 85 weight percent of the slurry.

7. The process of claim 1 wherein the evaporation occurs at a temperature which is higher than the boiling point of the alkyl halide but less than the temperature which would deleteriously affect the quality of the treated mixture.

8. The process of claim 4 wherein the evaporation temperature is within the range of from about 25° C. to about 45° C.

9. The process of claim 8 wherein the partially brominated diphenyl oxide contains hexabromodiphenyl oxide, heptabromodiphenyl oxide, octabromodiphenyl oxide, nonabromodiphenyl oxide and optionally either pentabromodiphenyl oxide, decabromodiphenyl oxide or both pentabromodiphenyl oxide and decabromodiphenyl oxide; and the methylene chloride comprises from about 40 weight percent to 85 weight percent of the slurry.

* * * * *